United States Patent [19]

Borzone et al.

[11] Patent Number: 5,122,134
[45] Date of Patent: Jun. 16, 1992

[54] SURGICAL REAMER

[75] Inventors: Rocco R. Borzone, Emerson, N.J.; Frank B. Gray, Knoxville, Tenn.

[73] Assignee: Pfizer Hospital Products Group, Inc., New York, N.Y.

[21] Appl. No.: 474,425

[22] Filed: Feb. 2, 1990

[51] Int. Cl.$^5$ .............................................. A61B 19/00
[52] U.S. Cl. ........................................ 606/80; 606/79; 606/167; 606/170; 606/180; 407/30; 407/58; 407/59; 407/60; 408/48
[58] Field of Search .................. 606/79, 80, 81, 82, 606/83, 84, 85, 167, 168, 169, 170, 180, 182, 171; 408/48, 224, 201, 211, 703-708, 713; 433/102; 407/54, 56, 57, 59, 60, 62, 63, 64

[56] References Cited

U.S. PATENT DOCUMENTS

| 533,573 | 2/1895 | Wilkens | 606/180 |
| 930,477 | 8/1909 | Hudson | 606/170 |
| 3,495,483 | 2/1970 | Janik | 408/211 |
| 3,554,192 | 1/1971 | Isberner | 606/79 |
| 4,273,117 | 6/1981 | Neuhäuser . | |
| 4,538,989 | 9/1985 | Apairo et al. | 433/102 |
| 4,541,423 | 9/1985 | Barber . | |
| 4,586,497 | 5/1986 | Dapra et al. . | |
| 4,594,034 | 6/1986 | Maier | 408/211 |
| 4,706,659 | 11/1987 | Matthews et al. . | |
| 4,751,992 | 6/1988 | DiPiesopolo . | |
| 4,951,690 | 8/1990 | Baker | 606/80 |

FOREIGN PATENT DOCUMENTS 227508 5/1969 U.S.S.R. ................. 606/80

OTHER PUBLICATIONS

William H. Huelson, M. D., "A New Method of Performing Operations on the Skull"Feb. 1910.
Richards Manufacturing Co. Inc. Orthopedic Catalog No. 15, 1974, p. 50.
Stryker Intl; Catalog dated Jun. 1979 entitled "SurgiPower ®-the world's most complete line of powered surgical instruments".
Larry S. Matthews, M. D. & Steven A. Goldstein, Ph.D., "A New Intramedullary Reamer Design" Scientific Exhibit presented at the 51st Annual Meeting of American Academy of Orthopedic Surgeons, Atlanta, GA Feb. 9-14, 1984.

Primary Examiner—Stephen C. Pellegrino
Assistant Examiner—Glenn K. Dawson
Attorney, Agent, or Firm—Peter C. Richardson; Lawrence C. Akers; Raymond W. Augustin

[57] ABSTRACT

The cutting head for a surgical reamer has a leading end for insertion into a bone canal and a trailing end for attachment to a drive shaft. The cutting head has a cutting surface formed about an axis of rotation of the cutting head. The cutting surface is formed by the rotation of the cutting edges on a plurality of flutes spaced around the axis of rotation. Each cutting edge has a first portion spaced a predetermined radial distance from the axis of rotation at the tip portion and terminates at a terminating point which is at a greater radial distance from the axis of rotation than the starting point. The cutting edge on each flute has a second portion having a starting point at the trailing end of the cutting head which is at a second predetermined radial distance from the axis of rotation. The second portion extends axially towards the tip portion and terminates at a point at a greater radial distance from the axis of rotation than the starting point thereof. A third curved portion starts at the terminating point of the first portion and terminates at the terminating point of the second portion and intersects the first and second portions tangentially.

16 Claims, 3 Drawing Sheets

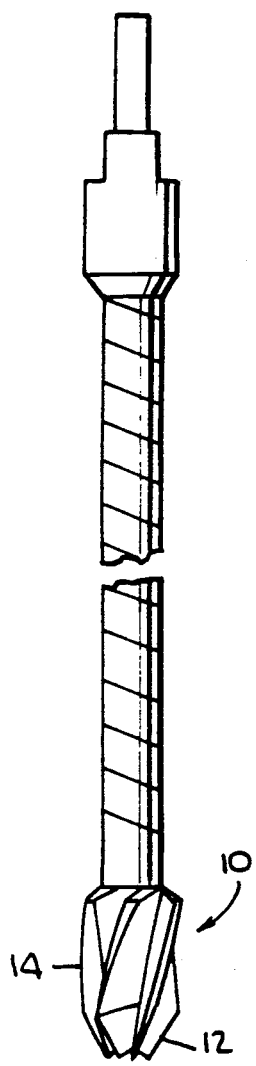
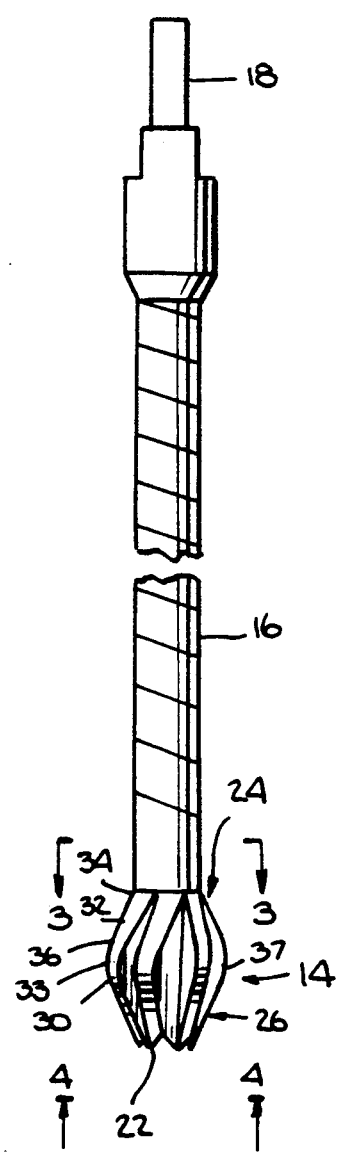
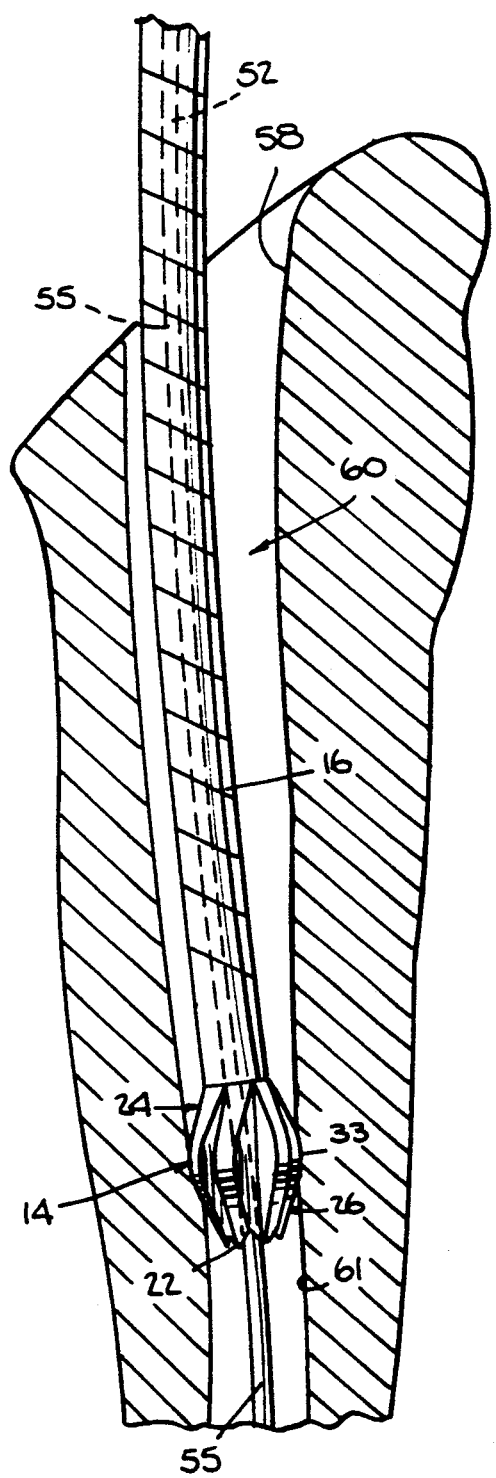
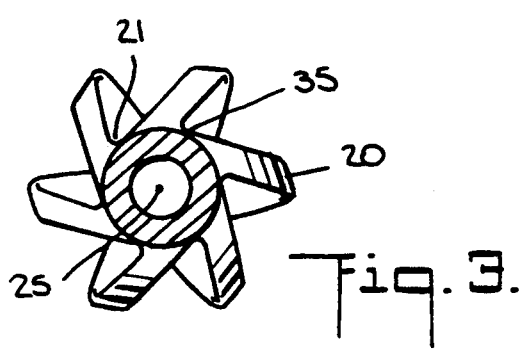

SURGICAL REAMER

BACKGROUND OF THE INVENTION

1. Field of the Invention

This invention relates to reamer cutting heads for surgical reamers used to enlarge bone canals during orthopedic surgery. More particularly, this invention relates to a cutting head which is easily adapted for use with a surgical reamer having a flexible drive shaft.

2. Description of the Prior Art

Surgical reamers are used in orthopedic surgery to enlarge medullary canals of long bones such as the femur and humerus in preparation for insertion of fixation devices, performing an intramedullary osteotomy, stimulating bone growth, the insertion of a plug to preclude bone cement from migrating while it is in the viscous state, and for other reasons. The medullary canals of bones are seldom straight. More typically, the canal will have some degree of curvature to it.

Should a straight and rigid series of reamers be employed to enlarge the canal, there is considerable likelihood that the reamer, in not being capable of following the bone's curvature, will jam or will not remove the desired uniform amount of bone tissue. In such a situation excessive tissue removal occurs in at least one plane as a reamer advances. For this reason, medullary canals are almost always prepared with reamers having a flexible shaft. Generally reamers for use with a flexible shaft utilize a central bore through both the reamer and drive shaft. The central bore is intended to receive a long, small diameter guide pin which is initially inserted into the medullary canal to act as a track for the advancing reamer. However, the use of a flexible shaft does not always solve the problem of excessive tissue removal and jamming.

The prior art cutting head design contributes to the history of intramedullary reamers jamming during use in long bones. When this jamming occurs with the prior art cutting head, the long guide pin has to be withdrawn from its position to assist in dislodging the reamer cutting head. This can result in a loss of reduction at the fracture site. Heretofore, the shape of the reamer cutting heads has been basically a cylinder with a short angled area towards the front that would do the cutting and another short angled area at the back of the head that is intended to facilitate the removal of the reamer. Such a cutting head is shown generally in U.S. Pat. No. 4,706,659, which issued to Matthews et al on Nov. 17, 1987. U.S. Pat. No. 4,751,992, which issued to A. DiPietropolo on Jun. 21, 1988, shows a cutting head on a shaft but does not refer to the design of the cutting head.

The cylindrical shape of the prior art cutting heads results in long flutes that produce friction and considerable heat while turning. This heat can be detrimental to the bone. The shape can also result in the reamer cutting a larger hole than desired as the reamer is directed away from its intended path of cutting, as when cutting a curved canal. As the reamer tilts or cants with respect to the canal, it cuts in a diagonal plane rather than a plane perpendicular to the canal. When a cylindrical cutting head is canted with respect to the internal bore and cuts a larger diameter than desired, jamming is likely to occur.

SUMMARY OF THE INVENTION

It is an object of the invention to provide a cutting head for a surgical reamer which doesn't jam and can easily follow a curved cutting path and can be easily withdrawn after the reaming operation.

It is yet another object of the invention to provide a cutting head for a surgical reamer which cuts very efficiently, thereby generating little heat and wear of the cutting head itself.

It is yet an additional object of the invention to provide a cutting head which is simple in design and economical to manufacture.

These and related objects are achieved in the present invention by a cutting head having a leading end for insertion into a bone canal and a trailing end at a predetermined axial distance away from the leading end and adjacent the drive shaft. The cutting head has a plurality of identical flutes spaced around the axis of rotation thereof, each terminating in a tip portion at one end of the cutting head and each having a trailing end opposite the tip portion. Each of the flutes has a cutting edge which, when rotated, forms the cutting surface of the reamer.

Each cutting edge and hence the cutting surface has a first portion spaced a predetermined radial distance from the axis of rotation at its starting point at the tip portion and terminates at a point a predetermined axial distance from the tip portion. The terminating point of the first portion is at a greater radial distance from the axis of rotation than the radial distance at its starting point. The cutting edge has a second portion having a starting point at the trailing end which starting point is at a second predetermined radial distance from the axis of rotation and extends axially towards the tip portion and terminates at a point at a greater radial distance from the axis of rotation than the starting point thereof. A third curved portion starts at the terminating point of the first portion and terminates at the terminating point of the second portion.

In alternate embodiments the first and second portions of the cutting surface may be in the form of a cone formed by the rotation of generally straight cutting portions on the cutting edge of each flute.

In another alternate embodiment the cutting surface is in the form of a surface of revolution formed by rotating a curvilinear arc formed on each of the flutes. Again, the arc has a starting point adjacent the tip portion and moves axially away therefrom at an increasing radial distance from the axis of rotation and forming an apex at a predetermined axial distance from the tip portion. Thereafter the arc extends axially away from the tip portion at a decreasing radial distance from the axis of rotation. It is contemplated that the curved cutting surface in the form of an arc may be a segment of an ellipse or a segment of a circle. The apex may be moved axially with respect to the tip portion in response to desired cutting parameters.

The cutting head has an axial bore therethrough concentric with the axis of rotation and a beveled counterbore extends radially and axially inwardly from the vertex of the tip portion. The beveled counterbore may have cutting surfaces formed thereon to enable the cutting head not only to enlarge an existing bore but start a new bore in a surface such as at the end of a long bone.

In the embodiment of the cutting head having the two conical portions, each cone intersects the axis of rotation at angles anywhere between 20° and 40°. The central ends of each conical surface tangentially intersects the intervening curved third portion to provide a smooth transition therewith.

Generally straight or helical V-shaped grooves extend between the flutes of the cutting head which grooves are so shaped that the flutes have a positive rake angle, generally about 7°.

These and other objects and advantages of the present invention will become apparent from the following description of the accompanying drawings, which disclose several embodiments of the invention. It is to be understood that the drawings are to be used for purposes of illustration only, and not as a definition of the invention.

BRIEF DESCRIPTION OF THE DRAWINGS

In the drawings wherein similar reference characters denote similar elements throughout the several views:

FIG. 1 is a prior art cutting head mounted on a flexible drive shaft;

FIG. 2 is side view of the cutting head of the present invention;

FIG. 3 is a plan view, partially in cross-section, of the cutting head of the present invention through line 3—3 of FIG.

FIG. 5 is a side view of the cutting head of the present invention mounted on a flexible reamer and reaming the medullary canal of a femur shown in cross-section;

DESCRIPTION OF THE PREFERRED EMBODIMENTS

Figure 6:
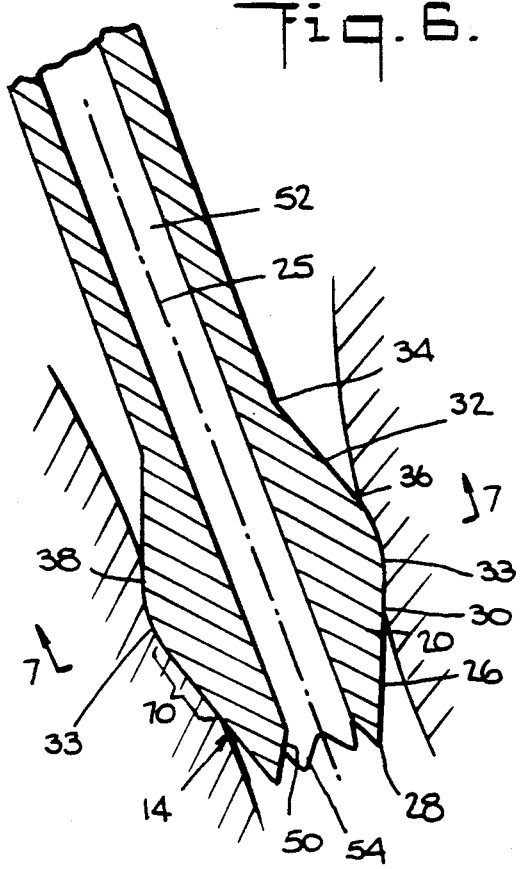
FIG. 6 is an enlarged cross-sectional view on a plane including the axis of rotation of the cutting head of the present invention within a medullary canal.

Referring to FIG. 1, there is shown a cutting head of the prior art generally denoted as 10. Prior art cutting head 10 has a conically shaped leading end 12 and a generally cylindrical trailing end 13.

Referring to FIGS. 2–8, there is shown the cutting head of the present invention generally denoted as 14. As is usual, cutting head 14 is rigidly connected to or integral with a drive shaft 16 which can be flexible in nature. Drive shaft 16 includes a drive connector 18 which may be connected to any suitable electrical or pneumatically powered tool (not shown).

In the preferred embodiment, the cutting head 14 includes a plurality of flutes 20 separated by generally V-shaped grooves 21 which extend from a leading tip portion 22 to a trailing portion 24 adjacent drive shaft 16. Flutes 20 may extend around cutting head 14 either in a helical fashion or may extend generally parallel to an axis of rotation 25. In the preferred embodiment the diameter of cutting head 14 at the termination of trailing end 24 is approximately the same diameter as drive shaft 16. Upon rotation about axis 25, cutting head 14 generates a cutting surface based on the shape of flutes 20. The number of flutes 20 (normally four to six) and their circumferential width is generally the same as in the prior art. As can be seen in FIGS. 2 and 5, the width of each flute 20 may widen as it extends from tip portion 22 to end 24.

Figure 8:
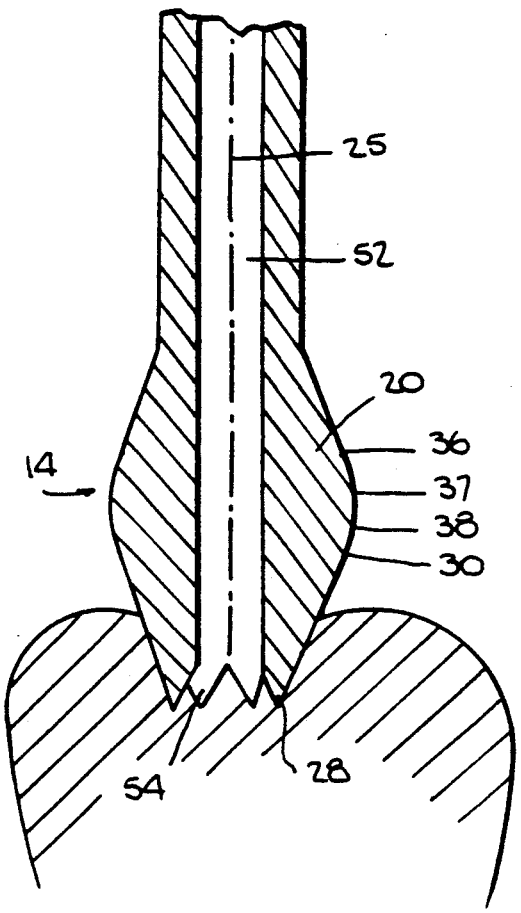
FIG. 8 is a cross-sectional view of the cutting head of the present invention engaging the end of a long bone and showing the teeth of the tip portion drilling a hole therein to be reamed.
Figure 4:
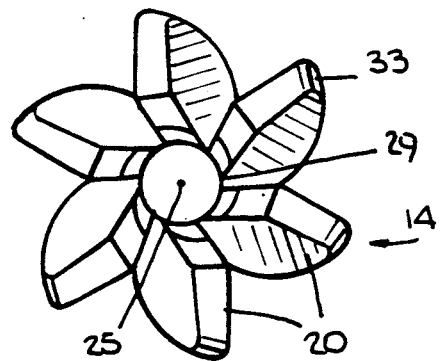
FIG. 4 is a bottom view of the cutting head of the present invention through line 4—4 of FIG. 2.

Referring to FIGS. 6 and 8, a preferred shape, in cross-section, of flutes 20 is shown. It can be seen that the preferred flutes have a cross-section formed by a first conical section 26 which extends from a starting point 28 at the tip portion 22 of cutting head 14 and extends radially outwardly to a terminating point 30 adjacent the apex or major diameter 33 of cutting head 14. Point 30 is located a predetermined axial distance from starting point 28 towards trailing portion 24. Thus cutting head 14 starts at a first predetermined diameter 29 at point 28 and increases in diameter to a larger diameter at point 30. Preferred cutting head 14 has a second conical portion 32 starting at a point 34 adjacent trailing end 24 of cutting head 14 which starting point 34 is spaced a predetermined axial distance from starting point 28 at tip 22. Conical surface 32 extends radially outwardly from starting point 34 to a terminating point 36. Thus cutting head 14 has a second predetermined diameter 35 at point 34 and increases in diameter to point 36. Neither the first and second predetermined diameters nor the diameters at points 30 and 36 have to be equal.

Cutting head 14 includes a third portion 38 which extends between the terminating point 30 of first conical portion 26 and terminating point 36 of second conical portion 32. The third portion 38 is either in the form of a sector of a sphere with its major diameter forming the apex 33 of the flute 20 or a torus with a sector of its outer surface forming the apex of the cutting surface. Major diameter 33 is, of course, larger than the diameters at points 30 and 36. In the preferred embodiment the conical portions 26 and 32 intersect with spherical or torodial sector 38 tangentially at terminating points 30 and 36 respectively, thereby forming a smooth transition surface with a maximum diameter at the apex 33.

Referring to FIGS. 3 and 6, it can be seen that the tip portion 22 at the leading end of cutting head 14 has an inwardly beveled portion 50 extending radially and axially inwardly towards a central bore 52 within cutting head 14 and a shaft 16. Teeth 54 are formed on each flute 20 adjacent the intersection of flutes 20 with tip portion 22. Central bore 52 receives the typical guide shaft 55 for aligning cutting head 14 within the bone canal.

Referring to FIG. 5, there is shown the reaming head 14 of the present invention used to enlarge a bore 58 within a medullary canal 60 of a femur 62. Referring to FIG. 8 it can be seen that teeth 54 of cutting head 14 allow the cutting head of the present invention to be used to start drilling the bore within the femur as well as to enlarge the bore. Without teeth 54 it would be impossible to start drilling a bore in a flattened surface.

Figure 7:
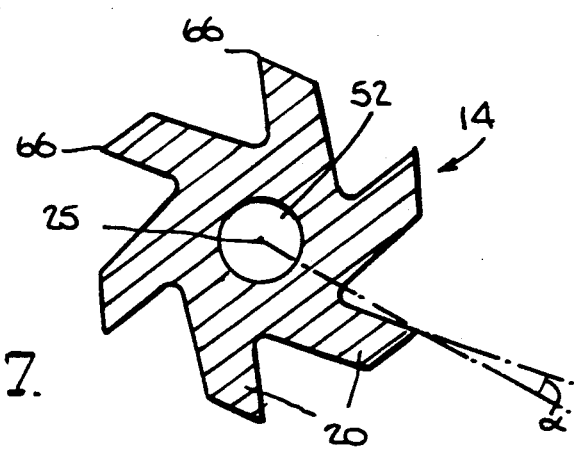
FIG. 7 is a cross-sectional view of the cutting head along line 7—7 of FIG. 6.

Referring to FIG. 7 there is shown a cross-sectional view of the cutting head of the present invention wherein a cutting edge 66 is formed on a leading side on each of flutes 20. Each cutting surface 66 is in the form of an arc with the shape described above with reference to FIG. 6 so that when high speed rotation of the reaming device occurs, a cutting surface as described above is formed (two cones with a spherical or torodial sector in between). The preferred angular orientation of cutting edge 66 with respect to a radial line through the axis of rotation 25 is such as to produce a positive rake angle α of approximately 7°. Although other rake angles could be used, a positive rake angle ensures efficient, low temperature cutting of bone within the canal.

Figures 9, 10:
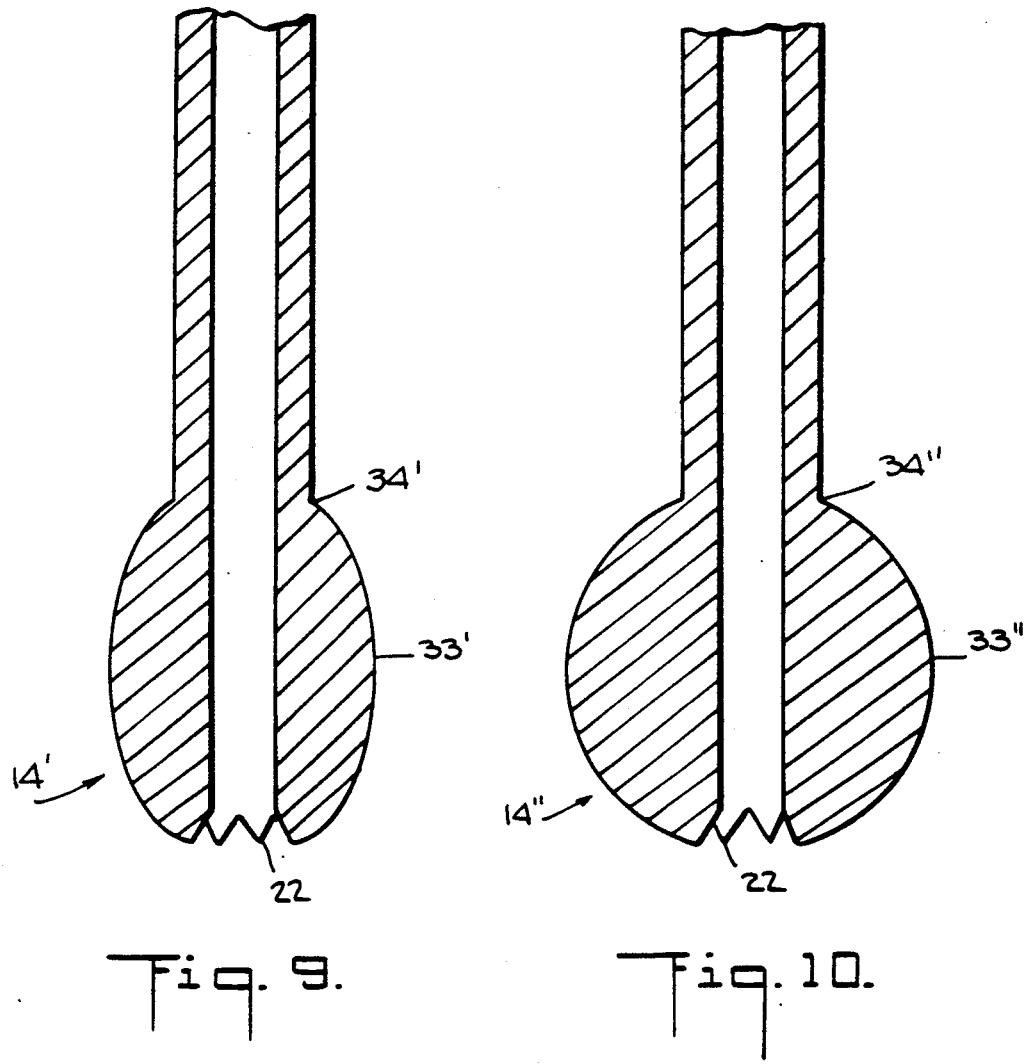
FIG. 9 is a cross-sectional view of an alternate embodiment of the cutting head of the present invention with a generally elliptical cutting surface.
FIG. 10 is still another alternate embodiment of the present invention showing a cutting surface with a generally circular cross-section.

FIGS. 9 and 10 show two alternate embodiments wherein instead of the cutting surface or cutting edge 66 being formed by the rotation of a cutting head 14 having two conical portions at the leading and trailing end with a central spherical or torodial portion the cutting heads have pure curvilinear or arced cutting surfaces from the tip portion to the trailing end of cutting head 14. FIG. 9 shows a cross-section of a cutting head 14' wherein the cutting edge of the flutes has the general form of an ellipse forming, on rotation, an ellipsoidal cutting surface. Similarly, the cross-section of the cutting head 14'', shown in FIG. 10, discloses a cutting surface formed by the rotation of a circular cutting edge which would form a spherical cutting surface. Clearly other arc forms can be used to produce a cutting surface as described.

It can be seen that the already described cutting head profile, wherein the cutting head forms a cutting surface having a first predetermined diameter at the tip portion and a larger major diameter 33 at the apex, which apex is spaced a predetermined axial distance from tip portion 22, and then deceasing in radial distance from the axis of rotation towards starting points 34' and 34'' at the trailing end of cutting heads 14' and 14'' fits all the above described embodiments. This geometry ensures the ability of the cutting head to cut a bore having the size of the major diameter at apex 33, 33' and 33'', no matter what orientation axis of rotation 25 of the cutting head takes with respect to the axis of bore 60.

Typical dimensions for the cutting head 14 of the present invention include a major diameter of between 0.25 and 1.0 inches and an overall length (from point 28 to point 34) of between 0.25 to 1.5 inches with the diameter of the tip portion being approximately 0.25 inches. If the curved apex area of the cutting surface is formed by the outer surface of a torus, the diameter of the torus is preferably about 0.25 inches regardless of the major diameter of the cutting head. Thus the center of the toroidal section at any point would not coincide with the axis of rotation unless the major diameter were 0.5 inches.

The utilization and operation of cutting head 14 will now be briefly described with reference to FIGS. 5-8. If one wishes to enlarge a bore 58 within a medullary canal 60, one would choose a cutting head having a major diameter 33 slightly larger than an existing bore 61. Cutting head 14 would either be integral with flexible drive shaft 16 or be attachable thereto for rotation therewith. Head 14 would then be inserted within the canal with bore 52 receiving guide shaft 55. The reamer would follow guide shaft 55 to enlarge bore 61. Should cutting head 14 be canted with respect to the preferred cutting path, the diameter 58 will be no larger than the major diameter 33 of the outing head.

In the unlikely event that outing head 14 would jam within bore 58, head 14 may be backed out slightly and, because of the relief provided by second portion 32, which has a decreasing diameter, cutting head 14 would easily work free so that the reaming operation can again proceed.

It has been found that the cutting head operates best if first and second conical portions 26, 32 are inclined with respect to axis of rotation 25 at an angle of between 20 and 40°. With these angles, the reaming and backing off of the reamer can be easily accomplished and with only a small production of cutting heat during reaming. This advantage occurs because the cutting chips formed are efficiently carried by generally V-shaped groove 21 away from the area of the apex 33 of the cutting surface. This is because the bone is cut along the short cutting length 70 of the flute in the area of the apex and the decreasing diameter of the cutting surface toward trailing end. The decreasing diameter of portion 32 allows the bone chips to move out of engagement with the surface of the bore being reamed and the flutes.

In the preferred embodiment, the angle that the first conical portion 26 forms with axis of rotation 25 is equal to the angle formed by second conical portion 32 with axis 25. In addition, the major diameter 33 of cutting head 14 is located at a greater axial distance from starting point 28 than the midpoint between points 28 and 34. Thus conical section 26 is longer than conical section 32 and therefore providing a longer cutting surface 70. Cutting length 70 can be varied by changing the angles of conical portions 26.

It should also be noted that, unlike the prior art, only small length 70 of the first portion 26 does the cutting as the bore is enlarged. In the prior art, the long cylindrical flutes maintain contact with the cutting chips and create heat by the friction of the reamer burning in the bore and the rubbing of the chips against the flutes.

While several examples of the present invention have been described, it is obvious that many changes and modifications may be made thereunto, without departing from the spirit and scope of the invention.

We claim:

1. A cutting head for a surgical reamer of the type having a series of circumferentially spaced flutes extending from a leading end of the cutting head, said leading end for insertion into a bone, to a trailing end of the cutting head, each flute having a cutting edge thereon generating upon rotation a surface of revolution formed about an axis of rotation of the cutting head, said cutting edge of each flute comprising:
   a curved central portion intermediate the leading and trailing ends of said cutting head formed as a sector of a torus;
   a first section extending in a straight line from a point at a first radial distance from said axis of rotation adjacent the leading end of the cutting head to a point of intersection on said central portion at a second radial distance from said axis of rotation, said second radial distance being larger than said first radial distance, said straight line of said first section forming a tangent with said sector of a torus at said first point of intersection; and
   a second section extending in a straight line from a point at a third radial distance from said axis of rotation adjacent the trailing end of the cutting head to a first point of intersection on said central portion at a fourth radial distance from the axis of rotation, said fourth radial distance being greater than said third radial distance, said curved central portion being disposed at a greater radial distance from said axis of rotation than said second and fourth distances, said straight line of said second section forming a tangent with said sector of a torus at said second point of intersection.

2. The cutting head as set forth in claim 1 wherein each flute has a predetermined circumferential width along said surface of revolution which widens from an end thereof adjacent said leading end of said first section to said trailing end of said second section.

3. The cutting head as set forth in claim 1 wherein said flutes extend generally parallel to the axis of rotation of the cutting head.

4. The cutting head as set forth in claim 1 wherein said flutes extend around the axis of rotation in a helical fashion.

5. The cutting head as set forth in claim 1 wherein said cutting head has a bore therethrough concentric with the axis of rotation.

6. The cutting head as set forth in claim 1 wherein said surface of revolution of said first section defines a plane at the leading end of the cutting head generally perpendicular to the axis of rotation, said cutting head having an axial bore therethrough, and wherein a beveled counterbore extends radially inwardly to said bore from said first radial distance on said plane at a predetermined angle.

7. The cutting head as set forth in claim 1 wherein said first and second sections extend from the first and third distances respectively to said tangential intersections at said respective second and fourth distances with said central portion at predetermined angles with respect to the axis of rotation.

8. The cutting head as set forth in claim 7 wherein said predetermined angles are between 20° and 40°.

9. The cutting head as set forth in claim 1 wherein a plurality of grooves extend radially inwardly from said cutting surface to define a plurality of flutes.

10. The cutting head as set forth in claim 9 wherein each of said plurality of grooves extend radially inwardly at an angle converging with the axis of rotation upon movement along said groove from said central portion of said cutting surface to toward the leading end of the cutting head.

11. The cutting head as set forth in claim 9 wherein said grooves extend axially in a direction generally parallel to the axis of rotation.

12. The cutting head as set forth in claim 9 wherein each of said grooves has a generally V-shaped cross-section.

13. The cutting head as set forth in claim 12 wherein said generally V-shaped cross-section of said groove forming said flutes has a positive rake angle.

14. A cutting head for a surgical reamer of the type having a leading end for insertion into a bone, a trailing end and a plurality of flutes extending from the leading end to the trailing end of the cutting head, a surface of revolution formed by the flutes upon rotation of the cutting head about an axis of rotation of the cutting head, said surface comprising:

a central portion formed by the rotation of a curvilinear arc;

a first section having a conical shape generated by the rotation of a first straight line extending from a point at a first radial distance from said axis of rotation adjacent the leading end of the cutting head to a first point of intersection on the central portion at a second radial distance from the axis of rotation, said second radial distance being larger than said first radial distance, said straight line of said first section tangent with said curvilinear arc of said central portion at said first point of intersection; and a second section having a conical shape generated by the rotation of a first straight line extending from a point at a third radial distance from the axis of rotation adjacent the trailing end of the cutting head to a second point of intersection on the central portion at a fourth radial distance from the axis of rotation, said fourth radial distance being greater than said third radial distance, said central portion being disposed at a greater radial distance from said axis of rotation than said second and fourth distances, said straight line of said second section forming a tangent with said curvilinear arc of said central portion at said second point of intersection.

15. The cutting head as set forth in claim 14 wherein said curvilinear arc is a sector of a sphere.

16. The cutting head as set forth in claim 14 wherein said curvilinear arc is a sector of a torus.

* * * * *